United States Patent [19]

Horwath et al.

[11] Patent Number: 4,605,619
[45] Date of Patent: * Aug. 12, 1986

[54] PROCESS FOR PREPARING FRUCTOSE FROM STARCH

[75] Inventors: Robert O. Horwath, Westport; Robert M. Irbe, Norwalk, both of Conn.

[73] Assignee: Nabisco Brands, Inc., Parsippany, N.J.

[*] Notice: The portion of the term of this patent subsequent to Jul. 3, 2001 has been disclaimed.

[21] Appl. No.: 592,123

[22] Filed: Mar. 22, 1984

Related U.S. Application Data

[63] Continuation-in-part of Ser. No. 393,589, Jun. 30, 1982, Pat. No. 4,458,017.

[51] Int. Cl.$^4$ .................. C12P 19/24; C12N 9/30; C12N 9/34; C12N 9/92; C12R 1/645

[52] U.S. Cl. .................. 435/94; 435/203; 435/205; 435/234; 435/911

[58] Field of Search ................... 435/94, 234

[56] References Cited

U.S. PATENT DOCUMENTS 4,431,733 2/1984 Horwath et al. ............... 435/94
4,458,017 7/1984 Horwath et al. ............... 435/94

*Primary Examiner*—Lionel M. Shapiro

[57] ABSTRACT

Process for preparing fructose by treating starch with alpha-amylase, contacting the resulting liquefied starch with glucoamylase to hydrolyzed said starch to glucose, and isomerizing at least part of the resulting glucose to fructose by contacting said glucose with glucose isomerase. The three enzymes are obtained from organisms of the Basidiomycetes class of fungi.

7 Claims, No Drawings

PROCESS FOR PREPARING FRUCTOSE FROM STARCH

CROSS REFERENCE TO RELATED APPLICATIONS

This application is a continuation-in-part of U.S. application Ser. No. 393,589, filed June 30, 1982, now U.S. Pat. No. 4,458,017, issued July 3, 1984.

BACKGROUND OF THE INVENTION

This invention relates to enzymatic processes for liquefying starch and converting the liquefied starch to glucose (dextrose) which can then be converted to fructose (levulose).

Most food grade glucose is provided as an enzymatic hydrolysate of corn starch, i.e., the corn syrup of commerce. Glucose is generally rated at being 60-80% as sweet as sucrose and therefore sells at a correspondingly lower price. It has long been known to isomerize glucose to fructose which is even sweeter than sucrose by employing an enzyme having glucose isomerase activity, preferably one which has been immobilized upon an inert support such as diethylaminoethyl-cellulose, porous glass or chitin. The isomerization of glucose provides an equilibrium mixture typically containing 42-55% fructose and is referred to as high fructose corn syrup (HFCS).

It is known that alpha-amylase, glucoamylase and glucose isomerase can be isolated from a substantial number of bacteria including species of Streptomyces, Bacillus, Acetobacter, Norcardia, Lactobacillus, Ampullariella, and various other genera of bacteria, and the enzymes have been employed in the commercial production of fructose from starch by known enzymatic techniques to provide mixtures of glucose and fructose. In the commercial process most commonly in present use, cornstarch is liquefied, enzymatically or chemically, and then treated with glucoamylase to produce glucose which is thereafter isomerized using glucose isomerase to mixtures containing both fructose and glucose. Higher concentrations of fructose are particularly desirable and may be obtained by the use of more active enzymes and/or the use of high isomerization temperatures.

Detailed descriptions of the enzymatic conversion of glucose to fructose employing glucose isomerase can be found in Hamilton, et al., "Glucose Isomerase: a Case Study of Enzyme-Catalyzed Process Technology", *Immobilized Enzymes in Food and Microbial Processes*, Olson, et al., Plenum Press, New York (1974), pp. 94–106, 112, 115–137; Chen, et al., "Glucose Isomerase (a Review)", *Process Biochem.*, (1980), pp. 36–41; Nordahl, et al., "Fructose Manufacture From Glucose by Immobilized Glucose Isomerase", *Chem. Abstracts*, vol. 82, (1975), Abs. No. 110316h; and Takasaki, "Fructose Production by Glucose Isomerase", *Chem. Abstracts*, vol. 81, (1974), Abs. No. 7647a. In addition, there are numerous patents relating to glucose isomerization of which U.S. Pat. Nos. 3,616,221, 3,623,953 (Reissue 28,885), 3,694,313, 3,708,397, 3,715,276, 3,788,945, 3,909,354, 3,960,663, and 4,308,349 are representative.

Because of the economics involved in producing glucose isomerase, it is of the utmost importance to use the isomerase under conditions whereby maximum yields of fructose are produced using minimum quantities of glucose isomerase. Moreover, the conditions for isomerization should be such that minimal quantities of objectionable by-products are produced.

SUMMARY OF THE INVENTION

It has now been surprisingly discovered that fungi of the class Basidiomycetes produce significant quantities of alpha-amylase, glucoamylase and glucose isomerase. Particularly useful genera include: Stereum, Perenniporia, Sebacina and Irpex. In particular, species of Irpex accumulate not only glucose isomerase activity which is produced in the mycelia of these organisms, but also alpha-amylase and glucoamylase which are extracellular and, therefore, accumulate in the nutrient medium. One can readily separate the glucose isomerase from the other two enzymes by merely filtering the cells. The mycelia can be employed in the enzymatic reaction mixture as a source of glucose isomerase or the enzyme activity can be separated from the mycelia by known methods after harvesting the mycelia from the medium in which grown. The glucose isomerase can then be separated from the mycelia by the usual extraction techniques, e.g., using sonic treatment or chemical lysing, or alternatively, the mycelia can be used directly. Of course, to avoid needless expense, the nutrient medium containing alpha-amylase and glucoamylase can be used as the source of the enzymes or, if desired, the enzymes can be separated from the nutrient medium and one from the other by using known techniques, e.g., column adsorption of the nutrient medium containing enzymes followed by selective elution of each enyzme.

In addition to the aforementioned microorganisms, the present invention contemplates the use of mutants and variants thereof as well as genetically transformed microorganisms derived therefrom by introduction of the enzyme genes into other microorganisms, including mesophilic and preferably thermophilic microorganisms. In addition, the isolated genes can be mutated to improve the properties of the respective enzymes with which they are associated. For example, the glucose isomerase gene can be mutated. The mutated glucose isomerase genes selected for such use are those which provide glucose isomerase which is stable at elevated temperatures, especially above 90° C. and preferably up to about 110° C. Such genes can be prepared by the usual techniques used for mutation of microorganisms such as irradiation or chemical means. Thus, isolated glucose isomerase genes which produce glucose isomerase of moderate thermal stability, on in vitro mutagenesis will undergo mutation, and selection of the appropriate mutated genes is accomplished by reintroduction of the mutated gene into either the parent or other organism, preferably a thermophilic organism followed by replication of the organism and testing of the thermal stability of the resulting glucose isomerase.

DESCRIPTION OF THE PREFERRED EMBODIMENTS

In the present invention, starch is liquefied by the action of alpha-amylase, hydrolyzed by employing glucoamylase to obtain glucose, and the glucose is enzymatically isomerized by glucose isomerase to fructose. The three enyzmes utilized herein are produced by the same microorganism of the class Basidiomycetes.

The starch starting material of this invention is obtained from cereal grains such as corn, milo, wheat, rye, and the like, and amylaceous roots and tubers such as potatoes, yams, carrots, cassava (manioc), and the like.

In the United States, cornstarch is especially preferred due to its comparatively low cost and ready availability.

Since all three enzymes may be produced by the same microorganism, fructose can be obtained from starch in a single batch reactor by the mere expediency of adding the Basidiomycetes mycelia to the reactor in which the alpha-amylase and glucoamylase conversion were carried out or in a separate reactor after glucoamylase conversion is completed.

Starch can be liquefied with alpha-amylase by any of the art-recognized procedures. Since the production of food grade glucose favors the use of enzymatic starch hydrolysis procedures, such procedures are preferred herein. Enzyme hydrolysis methods are described in U.S. Pat. Nos. 4,017,363, 3,912,590, 3,922,196, 3,922,197-201 and 4,284,722, the disclosures of which are incorporated by reference herein.

The liquefied starch is hydrolyzed to glucose by glucoamylase by procedures known to those familiar with the art. For example, the hydrolysis generally occurs at a somewhat lower temperature than the liquefication of starch, e.g., within the range of 55° C. to 60° C., at a pH between 4.0 and 5.0, with 0.3-1.0% of glucoamylase (based on the weight of starch) and for about 15 to 75 hours to provide a glucose-containing solution of a high level of purity, e.g., 97-98% of glucose.

Glucose can be isomerized to fructose in accordance with the present invention employing any of the known procedures, including contacting glucose solutions with whole cells, or passing the solutions through a bed containing bound, or immobilized, glucose isomerase. Materials and procedures used for the immobilization of enzymes are well known and are described in a number of publications including Wang, et al., *Fermentation & Enzyme Technology*, John Wiley & Sons, Inc., New York (1979), pp. 318-338 and Kirk-Othmer, *Encyclopedia of Chemical Technology*, 3rd Ed., John Wiley & Sons, Inc., New York (1980), vol. 9, pp. 148-172, the disclosures of which are incorporated herein.

Particularly preferred species of the aforesaid alpha-amylase, glucoamylase and glucose isomerase producing Basidiomycetes for use in the present invention are *Stereum striatum*, ATCC No. 20633; *Perenniporia compacta*, ATCC No. 20636; *Sebacina colcea*, ATCC No. 20638 and *Irpex mollis*, ATCC No. 20634. Cultures of strains of those preferred species of fungi were deposited with the American Type Culture Collection, 12301 Parklawn Drive, Rockville, Md. 20852, on June 28, 1982, where the organisms were accorded the indicated accession number, i.e., ATCC number.

The determination of other alpha-amylase, glucoamylase and glucose-isomerase producing fungi of the Basidiomycetes class can be carried out using simple test procedures. Cultures of the test organism are incubated for 7 days at 25° C. with vigorous shaking in a growth medium containing cornsteep liquor, magnesium sulfate, potassium phosphate, xylose and agar in shake flasks. The cells are then separated from the nutrient medium by known methods, e.g., filtration, and the nutrient medium is tested for alpha-amylase and glucose isomerase activity by simply adding starch to one portion of the nutrient medium and testing for liquefied starch, and adding liquefied starch to another portion of the nutrient medium and testing for the presence of glucose. The filtered mycelia are then checked for the desired enzyme activity by analysis of the enzymatic reaction solutions produced with the various substrates and determination of the presence of, for example, glucose or fructose. Fructose is identified by standard determination methods such as the acid carbazol-cysteine test or xylulose determination methods using gas chromatography or high pressure liquid chromatography.

Using these test procedures, or obvious modifications thereof, various additional species of fungi can be tested to determine the presence of the desired enzyme activities.

The selected fungi can be grown in accordance with known methods of propagation. One such method employs xylose as the carbohydrate source as well as other ingredients usually present in such media such as cornsteep liquor, inorganic salts, and the like.

After growth for a sufficient period of time, e.g., to about 120 hours, the mycelia are harvested usually be filtration followed by washing with water buffered to a pH in the range of 6 to 7. The nutrient medium is reserved for alpha-amylase and glucoamylase activity and, if desired, the enzymes may be extracted from the nutrient medium. The glucose isomerase is then extracted from the mycelia. A convenient method of extraction involves sonic treatment or cell homogenization of aqueous mycelia suspensions in the presence of glass beads with cooling. The extracts formed can be purified employing standard techniques such as column chromatography. The enzyme extract can now be used in the isomerization reaction. Alternatively, as previously mentioned, the mycelia can be used as the source of the enzyme in the isomerization mixture.

In order to describe more clearly the nature of the present invention, a specific example will hereinafter be described. It should be understood, however, that this is done solely by way of example and is intended neither to delineate the scope of the invention nor limit the ambit of the appended claims.

EXAMPLE

Preparation of alpha-amylase, glucoamylase and glucose isomerase

*Irpex mollis*, ATCC No. 20634, was grown in accordance with the following:

A. Culture Maintenance: After incubating the cultures on malt agar slants for 7 days at 30° C., the isolates were inoculated into shaker flasks or maintained under refrigeration (about 10° C.).

B. Shake Flask Propagation: Inoculation medium was made up as follows:

| Ingredient | % By Weight |
| --- | --- |
| Cornsteep liquor | 2.0 (d.b.) |
| Xylose | 5.0 |
| $KH_2PO_4$ | 0.1 |
| $MgSO_4.7H_2O$ | 0.15 |
| Agar | 0.4 |
| adjust pH to 6.5 | |

80 Ml aliquots of the above medium were placed in 500 ml Erlenmeyer flasks together with 20 ml of a 25% glucose solution (sterilized) for the inoculum fermentation and the flasks were brought to 80% of their volume with water purified by reverse osmosis. Production flasks were similarly charged except no agar was added.

First Stage (test tube) Propagation

In a sterile hood, approximately one half of the mycelia from a slant is transferred with a metal loop to a test tube with 10 ml of the inoculation medium and about six 3 mm glass beads (sterile). The tubes are vortexed for 30–60 seconds or until the mycelia are disrupted. The tubes are then placed on a G-50 shaker at 200 rpm, 30° C., for 7 days.

Second Stage (inoculum) Propagation

After 7 days, 5 ml are transferred to a 500 ml Erlenmeyer shake flask, and 1 ml is transferred into brain heart infusion to check sterility. These inoculation flasks are placed on a G-50 shaker at 200 rpm, 30° C., for 7 days.

Third Stage (production) Propagation

After 7 days, 5 ml are transferred from the inoculation flask to several fermentation flasks. The fermentation flasks are placed on the G-50 shaker at 200 rpm, 30° C., for 9 days.

C. Harvesting Cell Biomass: After the 9-day incubation period, the pH of each shake flask was measured. the cell biomass was filtered and washed twice with pH 7.0 phosphate buffer. After the second filtration, the harvested cell biomass from each culture was weighed and frozen for bioconversion.

The nutrient medium containing alpha-amylase and glucoamylase was reserved and the enzymes were used in this form for the enzymatic conversion of starch to glucose.

D. Liquefication of Starch and Conversion of Glucose: An aqueous slurry of cornstarch containing a water-soluble calcium compound (molarity of from about 0.003 to about 0.03) was heated to gelatinize the starch. Thereafter, the mixture was cooled to about 50° C. to 55° C., filtered nutrient medium was then added and the mixture was maintained at about 50° C. until all the starch was liquefied and saccharified. The resulting mixture was maintained at this state until the desired D.E. was reached.

E. Isomerization of Glucose to Fructose:

1. Whole-cell Bioconversion: (under sterile conditions) Approximately 1 gram wet weight cells is placed into a 300 ml baffled flask containing 50 ml of glucose phosphate buffer (1% glucose added to the phosphate buffer w/v) and the suspension made 0.02M in NaF. The flask is placed on the G-50 shaker at 200 rpm, and samples are taken at 6, 12 and 24 hours by aseptically transferring 2 ml from the bioconversion flask to 15 ml Corning centrifuge tubes. The samples are centrifuged for 5 minutes, then 1 ml is removed and passed through a Sep-Pak $C_{18}$ cartridge (Waters Associates, Milford, MA) following which the filtrates were analyzed by high pressure liquid chromatography (HPLC).

2. Bioconversion by Cell-free Extracts: Mycelia (4 grams wet weight) in phosphate buffer (pH 6.5) are blended in a Waring blender at low speed for 15 seconds. The buffered homogenate is then transferred to a 50 ml glass Duran Sample Flask containing 50 grams (about 80% by volume) glass beads of a diameter of 0.45 to 0.5 mm. The chamber is then vigorously agitated with a Braun Mechanical Cell for 1 minute while cold carbon dioxide is allowed to flow past the chamber to minimize heating.

Alternatively, the low speed blended mycelia in buffer is placed in a plastic centrifuge tube in an ice bath and then sonicated with a Heat Systems Ultrasonics Cell Disrupter, Model 350, set at 50% duty cycle, output control at 6, continuous mode, in 5 cycles of 15 seconds on and 15 seconds off.

The filtered enzyme solution was used in the isomerization reaction.

The isomerization mixture containing 50 mmoles of glucose (maleate buffered to pH 6.7), $MgCl_2$ (10 mM), $Co^{+2}$ (1 mM) and enzyme solution (50 mg of protein) was incubated at 40° C. for 12 to 18 hours.

Assay of the mixture, actually aliquots thereof, showed the presence of fructose in addition to glucose. The assays employed were gas chromatography and the cysteine carbazole reaction.

F. Additional Genera: Employing the conditions described above, the following strains were also found to produce the three enzymes necessary to practice the instant invention: *Stereum striatum*, ATCC No. 20633; *Perenniporia compacta*, ATCC No. 20636; and *Sebacina colcea*, ATCC No. 20638.

What is claimed is:

1. The process for preparing fructose which comprises liquefying starch by contacting starch with alpha-amylase contacting the resulting liquefied starch with glucoamylase to hydrolyze said starch to glucose, and isomerising at least part of the resulting glucose to fructose by contacting said glucose with glucose isomerase, wherein all three enzymes are obtained from the same organism of the Basidiomycetes class of fungi.

2. The process according to claim 1 wherein the organism is a member of a genera selected from the group consisting of Stereum, Perenniporia, Sebacina and Irpex.

3. The process according to claim 2 wherein the organism is a species selected from the group consisting of *Stereum striatum, Perenniporia compacta, Sebacina colcea* and *Irpex mollis.*

4. The process according to claim 3 wherein the organism is selected from the group having the identifying characteristics of *Stereum striatum*, ATCC No. 20633; *Perenniporia compacta*, ATCC No. 20636; and *Sebacina colcea*, ATCC No. 26038.

5. The process of claim 1 wherein the glucose isomerase activity is present in the mycelia of the said organism.

6. The process of claim 1 wherein the glucose isomerase activity is extracted from the mycelia of the said organism.

7. The process of claim 1 wherein the glucoamylase and alpha-amylase activities are present in the nutrient medium employed for growth of the said organism.

* * * * *